United States Patent
Minotti et al.

(12) 
(10) Patent No.: US 6,461,337 B1
(45) Date of Patent: Oct. 8, 2002

(54) ELECTROSTATIC MICROACTUATORS, ACTIVE THREE-DIMENSIONAL MICROCATHETERS USING SAME AND METHOD FOR MAKING SAME

(75) Inventors: Patrice Minotti, Gennes; Gilles Bourbon, Besancon; Philippe Langlet, Festubert, all of (FR); Takahisa Masuzawa; Hiroyuki Fujita, both of Tokyo (JP)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/555,892
(22) PCT Filed: Dec. 3, 1998
(86) PCT No.: PCT/FR98/02613
  § 371 (c)(1),
  (2), (4) Date: Jul. 28, 2000
(87) PCT Pub. No.: WO99/30410
  PCT Pub. Date: Jun. 17, 1999

(30) Foreign Application Priority Data

Dec. 5, 1997 (FR) .............................. 97 15393

(51) Int. Cl.[7] .......................... A61M 25/00; H21N 1/00
(52) U.S. Cl. ................. 604/264; 310/20; 310/40 MM; 310/309; 318/135; 604/21
(58) Field of Search .......................... 604/264, 21, 20, 604/508; 310/309, 20, 17, 15, 40 MM; 318/135

(56) References Cited

U.S. PATENT DOCUMENTS

| | | | |
|---|---|---|---|
| 5,235,225 A | | 8/1993 | Colgate et al. ............... 310/12 |
| 5,563,466 A | | 10/1996 | Rennex et al. ............... 310/309 |
| 5,771,902 A | * | 6/1998 | Lee et al. ................... 128/897 |
| 5,819,749 A | * | 10/1998 | Lee et al. ................... 128/899 |
| 6,013,033 A | * | 1/2000 | Berger et al. ............... 600/466 |

OTHER PUBLICATIONS

Akiyama et al.; Controlled Stepwise Motion in Polysilicon Microstructures; J. Microelec. Sys., vol. 3, No. 3, pp. 105–110 (1993).

Akiyama et al.; Scratch Drive Actuator with Mechanical Links for Self–Assembly of Three–Dimensional MEMS; J. Microelec. Sys., vol. 6, No. 1, pp. 10–17 (1997).

Ming et al.; Self–Assembled Microactuated XYZ Stages for Optical Scanning and Alignment; 66–147D Engineering IV, Los Angeles, CA, Sandia National laboratories, Albuquerque, New Mexico.

(List continued on next page.)

*Primary Examiner*—Gregory L. Huson
*Assistant Examiner*—Kathleen J. Prunner
(74) *Attorney, Agent, or Firm*—Finnegan, Henderson, Farabow, Garrett & Dunner

(57) ABSTRACT

An electrostatic microactuator, known as a "Scratch Drive Actuator" or SDA, is based on a collective set of distributed elementary SDAs of small size that are associated with one another and that integrates a large number so as to allow the addition of the forces generated by each of the SDAs in the collective set. An external mechanical prestress, formed by a homogeneous external pressure in the form of a bias voltage applied at rest to the associated SDAs, is applied to the SDAs to allow a superposition of the forces generated by the associated SDAs. This is done while communicating to an external load the entire driving force emanating from the collective behavior of the SDAs. The electrostatic attraction forces established by the bias voltage are used to calibrate an individualized prestress for each actuator involved in the collective set. Such an electrostatic microactuator forms part of an active three-dimensional microcatheter, as one possible application, that can be used in a blood vessel.

40 Claims, 8 Drawing Sheets

OTHER PUBLICATIONS

Figure 1A:
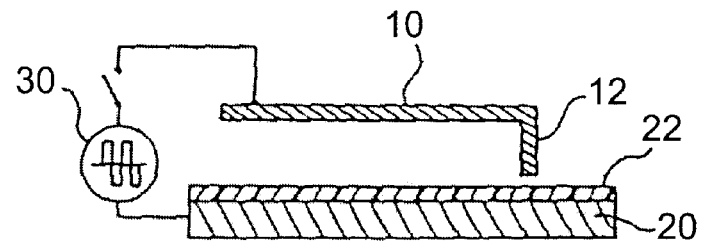

Fujita et al.; Group Work of Distributed Microactuators; Robotica, vol. 14, pp. 487–492 (1996).

Furuhata et al.; Array–Driven Ultrasonic Microactuators; Transducers, Conf. 6, pp. 1056–1059 (1991); Institute of Electrical and Electronics Engineers.

Fukuda et al.; Giant Magnetostrictive Alloy (GMA) Applications to Micro Mobile Robot as a Micro Actator without Power Supply Cables; Proceedings of the workshop on micro electro mechanical systems investigation of micro structures, sensor, actuators, machines and robots; NARA JP Workshop 4 pp. 210–215 (1991).

Search reports from the PCT (PCT/FR98/02613) and French (97 15393) priority applications.

* cited by examiner

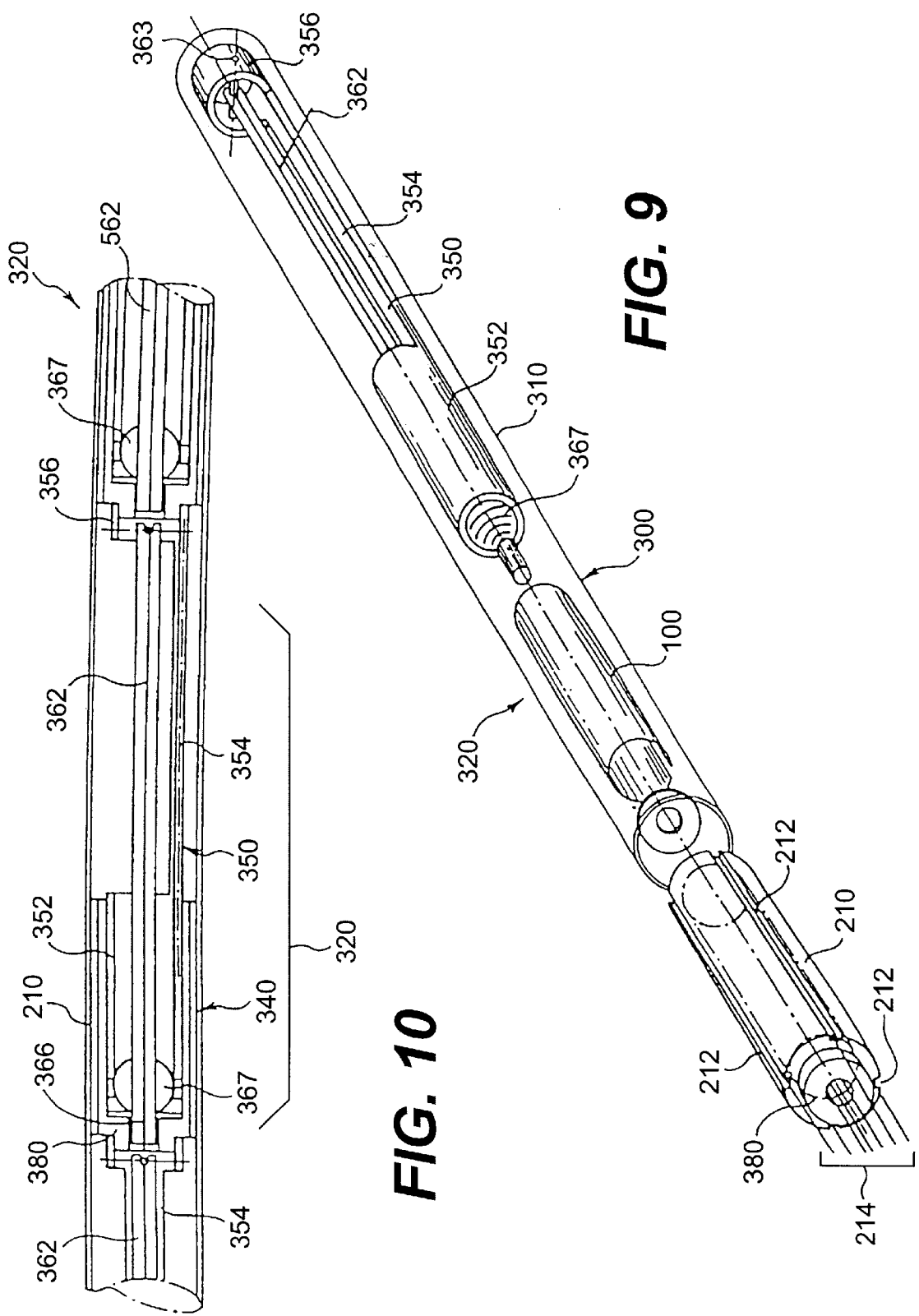

ELECTROSTATIC MICROACTUATORS, ACTIVE THREE-DIMENSIONAL MICROCATHETERS USING SAME AND METHOD FOR MAKING SAME

CROSS REFERENCE TO RELATED APPLICATIONS

This application is based on and claims the benefit of international application PCT/FR98/02613, filed on Dec. 3, 1998 and French application 97 15393, filed Dec. 5, 1997. The entire disclosure of these applications is relied upon and incorporated by reference herein.

The present invention relates to the field of electromechanical microactuators, that is to say the field of microsystems adapted for delivering a controlled mechanical force in response to an electrical excitation.

The document U.S. Pat. No. 5235225 describes a structure in which the basic actuator consists of two parallel stators each furnished with a plurality of electrodes and with a flexible rotor, which is at least partially electrically conductive and disposed between the two aforesaid stators. The displacement of the rotor is effected through sequential control, progressing in space, from an electric voltage applied to the electrodes.

More precisely still, the present invention relates to the field of electrostatic microactuators known as "Scratch Drive Actuators" or "SDAs". Specifically, the present invention relates to an electrostatic microactuator based on distributed elementary SDAs.

A description of these actuators will be found in the documents [1], [2] and [3].

These actuators proposed some years ago, are most particularly intended for the direct driving of micromachines of micrometer dimensions. They have the particular feature of associating a mechanism for transferring mechanical energy by friction with the conventional implementation of an electrostatic force field.

The aforesaid documents may usefully be referred to for a proper understanding of the general structure and the operation of these actuators.

The latter are shown diagrammatically in FIGS. 1A to 1D attached.

In essence, an SDA comprises a plate or beam (10), made for example of polysilicon, furnished at one end with a projecting strut or pad 12, directed toward a substrate 20, made for example of silicon, covered with an insulating layer 22, made for example of $Si_3N_4$. A generator 30 is adapted for applying voltage pulses between the plate 10 and the substrate 20.

Figure 1B:
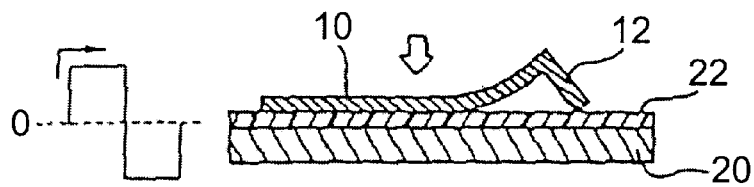

As may be seen in FIG. 1B, on a rising pulse edge, the plate 10 is drawn toward the substrate 20 by the electrostatic force generated between the latter. The bearing of the strut 12 on the layer 22 imposes a static flexion on the plate 10, which in turn gives rise to an offset of the strut 12.

Figure 1C:
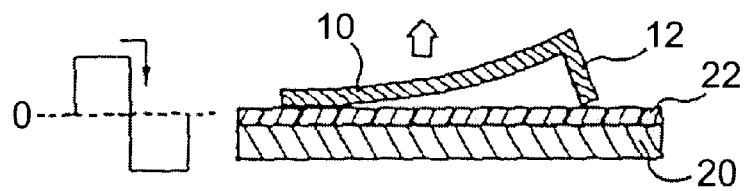
Figure 1D:
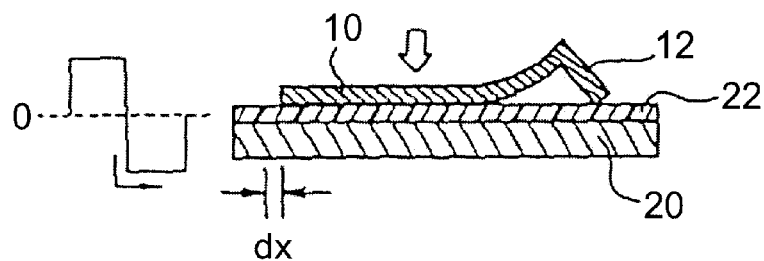

On the falling edge of the pulse, as may be seen in FIG. 1C, the plate 10 tends to revert to its rest geometry, by virtue of the elastic energy stored up in the plate 10, and has therefore been shifted by a flexion of the plate 10, which in turn gives rise to an offset of the strut 12.

On the falling edge of the pulse, as may be seen in FIG. 1C, the plate 10 tends to revert to its rest geometry, by virtue of the elastic energy stored up in the plate 10, and has therefore been shifted by an amplitude dx with respect to its former position, by reason of the bearing defined between the strut 12 and the layer 22.

Thus, these systems make it possible to convert mechanical oscillations of very small amplitude originating in the static flexion of the thin plate 10, into a rigid body motion of this same plate.

The lower the height of the strut 12 situated under the flexing plate 10, the stronger the electrostatic forces produced at the plate 10/substrate 20 interface, for a given excitation voltage emanating from the generator 30. The height of the strut 12 typically of the order of a micrometer, moreover introduces a high gearing reduction in the energy conversion mechanism at the plate 10/substrate 20 interface. The gearing reduction intrinsic in the very small mechanical deformations involved in energy conversion by friction, contributes to a dual increase in the driving forces generated during the displacement of the plate. SDAs thus have the particular feature of developing sizeable useful forces at low speed, in the absence of any auxiliary speed decrease.

The length of the displacement step depends on the height of the strut 12, on the stiffness of the plate 10 and on the control voltage applied. The displacement step is typically of the order of 25 nanometers for a plate 10 exhibiting a width of the order of 50 micrometers, a thickness of the order of 1 micrometer and a length of the order of 60 micrometers.

The repeating of such cycles makes it possible to accumulate displacement steps and consequently allows a sizeable relative displacement between the plate 10 and the substrate 20.

However, although they are showing themselves to be very promising, to the knowledge of the inventors, SDAs have hitherto remained on the laboratory scale and have not enjoyed industrial development.

This seems to be due in particular to the fact that the force generated by the known SDAs remains limited even if it is sizeable on the micrometer scale. This force, typically of the order of from 50 to 100 micro newtons for an SDA energized at a peak excitation voltage of the order of 100 V, can satisfy only a limited number of applications reserved exclusively for the micromachine scale.

Also, attempts to appreciably intensify this force by increasing the size of the SDAs have not been crowned with success hitherto.

Indeed, on the one hand the electrostatic forces involved in the actuation decrease very rapidly with increasing dimensions of the SDAs. On the other hand, the production processes involved in fabricating SDAs prevent the production of devices having a thickness greater than a few microns, which constitutes an intrinsic limitation to the increasing of the other dimensions of the SDA.

The object of the present invention is now to propose novel means making it possible to implement SDAs industrially.

Contrary to current attempts tending to increase the size of an SDA so as to obtain an acceptable output force, within the framework of the present invention it is proposed to retain SDAs of small size, but to increase their number and to associate them under suitable conditions so as to allow the addition of the forces generated by each of these SDAs, namely by using means adapted for, on the one hand, applying to said SDAs an external mechanical prestress able to allow a superposition of the forces generated by the various SDAs and, on the other hand, communicating to an external load the entire driving force emanating from the collective behavior of these same SDAs.

This mechanical prestress of the SDAs is advantageously obtained with the aid of a bias voltage applied at rest to the set of SDAs.

To allow the entire driving force emanating from the collective behavior of the SDAs to be communicated to an external load, according to an advantageous characteristic of the present invention, the sheet carrying the SDAs is placed in a mechanical clearance at the interface of two solid bodies articulated together.

The inventors have in fact demonstrated that such a prestress, associated with means guaranteeing the communication of the driving force, to the external load, was indispensable for allowing aggregation of the forces generated by the various SDAs.

The cooperation of microactuators has already been utilized in the field of the motorization of micromachines but, to the knowledge of the inventors, only via the development of conveyors of objects by friction in the horizontal plane, so as to profit from the gravity of the displaced object. With such devices, the driving forces communicated to the movable element depend only on the mass of the displaced object, as well as on the coefficient of friction at the object/actuators interface (in accordance with Coulomb's laws of solid friction). In this case the driving forces communicated to the displaced object are unaffected both by the number and by the driving characteristics of the actuators participating in the motorization. Moreover, these same driving forces depend on the configuration of the machine (or conveyor) in space and in particular on the horizontality of the object transfer plane. It is clear, consequently, that increasing the number of actuators participating in the motorization of one and the same load does not necessarily lead to a matching increase in the useful forces involved in the motorization.

The present invention is distinguished from the previous inventions in that it does not use gravity (or any other solution such as the elastic deformation of a bearing spring, etc.) to calibrate a prestress in the mechanical power transmission procedure. It uses electrostatic attraction forces which are particularly strong in view of the scale of the SDAs, to calibrate an individualized prestress for each actuator involved in the collectivity. This prestress is intrinsic to each actuator insofar as it is unaffected by the parameters of the displaced load, unlike the prior art devices which routinely involve gravity. The application of the prestress, within the framework of the present invention, is moreover natural since the electrostatic attraction does not require recourse to the elastic deformation of an auxiliary bearing spring. In practice, this deformation is obtained with the aid of a bias voltage applied at rest to the set of SDAs, as indicated earlier. Moreover, the electrostatic forces depend only on the relative position of the SDA on its substrate and are unaffected by the posture of the substrate in three-dimensional space.

The proposed invention consequently guarantees, unlike the collective devices of the prior art, effective superposition of the individual forces of each SDA, regardless moreover of the spatial configuration of the colony considered.

The inventors have moreover found that the support lattices proposed hitherto, and capable of associating several SDAs, turn out to be incapable of retaining their mechanical integrity during the transmission of sizeable external forces. These known lattices are generally formed of an assembly of extremely fragile beams having, like the SDAS, a thickness of the order of a micrometer (these being fabricated at the same time as the SDAs, in the course of the same procedure and from a similar material). The fragility of the known lattices is therefore an intrinsic limitation to the transmission of sizeable forces.

Thus, according to another advantageous characteristic of the present invention, contrary to current attempts, the inventors propose that flexible sheets, made for example of polysilicon, comprising a large number of SDAS, be inserted into a mechanical clearance separating two solid bodies articulated with respect to one another. This technical solution in fact allows a very large number of SDAs to be made to cooperate in practice under conditions promoting effective superposition of the driving forces and in such a way that the transmission of mechanical power, which results from the accumulating of the useful forces produced by the collectivity, may not be passed on to the hardware structure connecting the assembly of SDAs.

To this end, within the framework of the present invention, the SDA sheets advantageously consist of a framework, in contact solely with one of the solid bodies involved in the articulation, for example the bedplate. The SDAs are for their part only in exclusive contact with the other solid body involved in the articulation, for example the drive shaft. Such a configuration permits accumulation of force proportional to the number of SDAs involved in the interface. It also and above all guarantees the integrity of the framework (since the latter is reinforced on contact with the bedplate), regardless of the transmission of external mechanical power communicated to the movable element (or drive shaft).

The invention thus contributes, as a whole, to the physical and material (or mechanical) possibility of involving a very large number of SDAs in the driving of one and the same load, unlike in the case of the known prior art solutions.

Typically, a system in accordance with the present invention thus integrates from a few tens to a few thousand SDAs.

Moreover, the present invention proposes specific means for shaping a sheet, made for example of polysilicon, comprising a large number of SDAs, by flexion of bars integral with this sheet.

The present invention also relates to a process for shaping a sheet comprising a large number of SDAs, utilizing such means.

According to another advantageous characteristic of the present invention, the system can also comprise means forming a force sensor, for example a torque sensor, comprising at least one beam integrated into the sheet forming the SDAs and adapted to be deformed upon actuation of the system, said beam being associated with means for analyzing its deformation.

Figure 2:
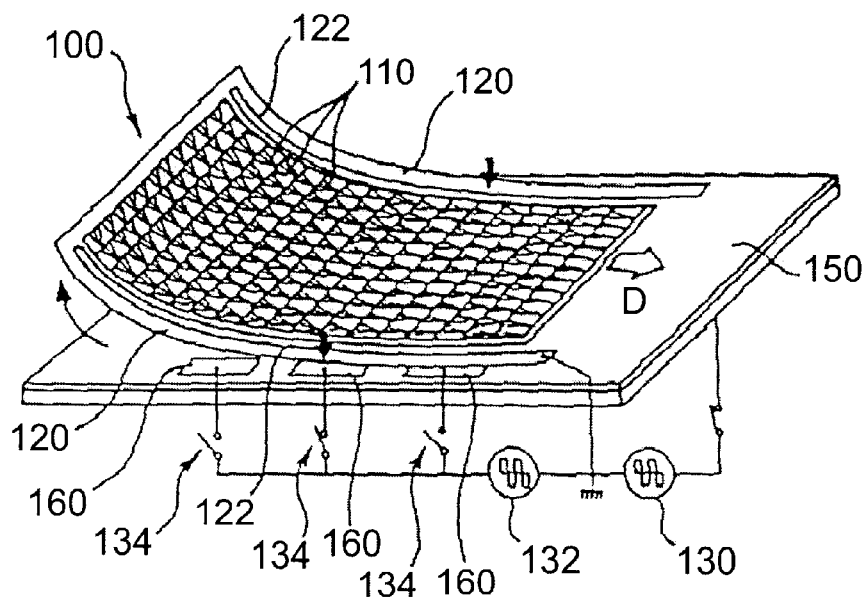
Figure 3:
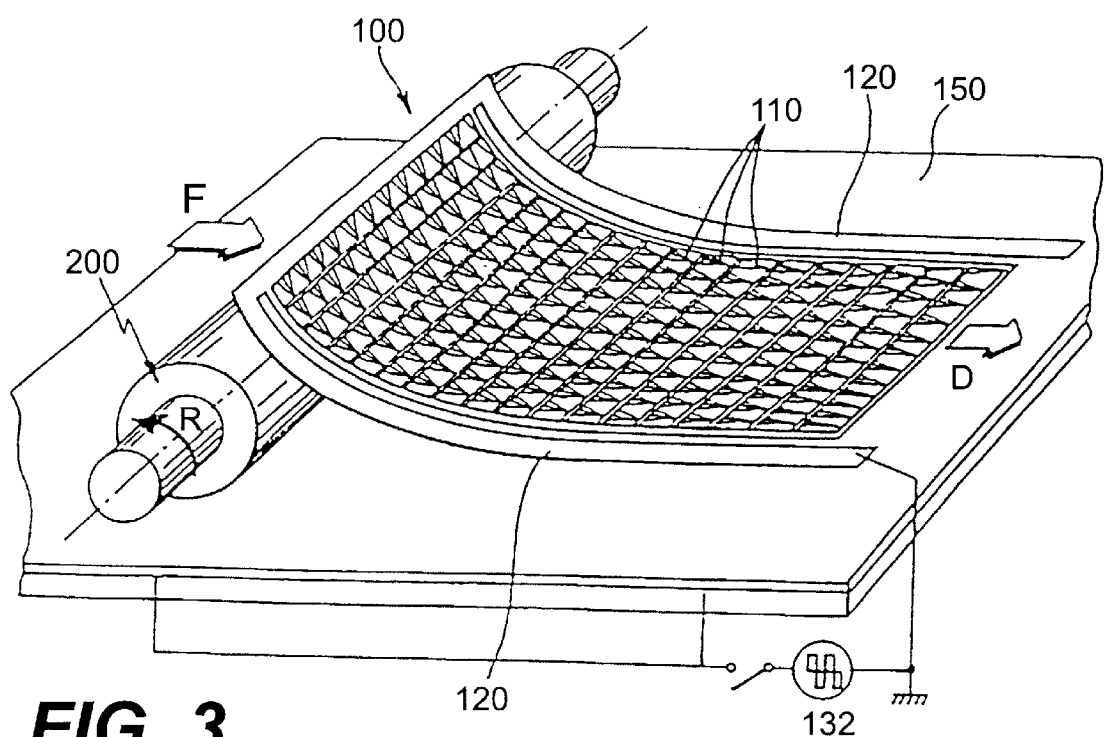
Figure 4:
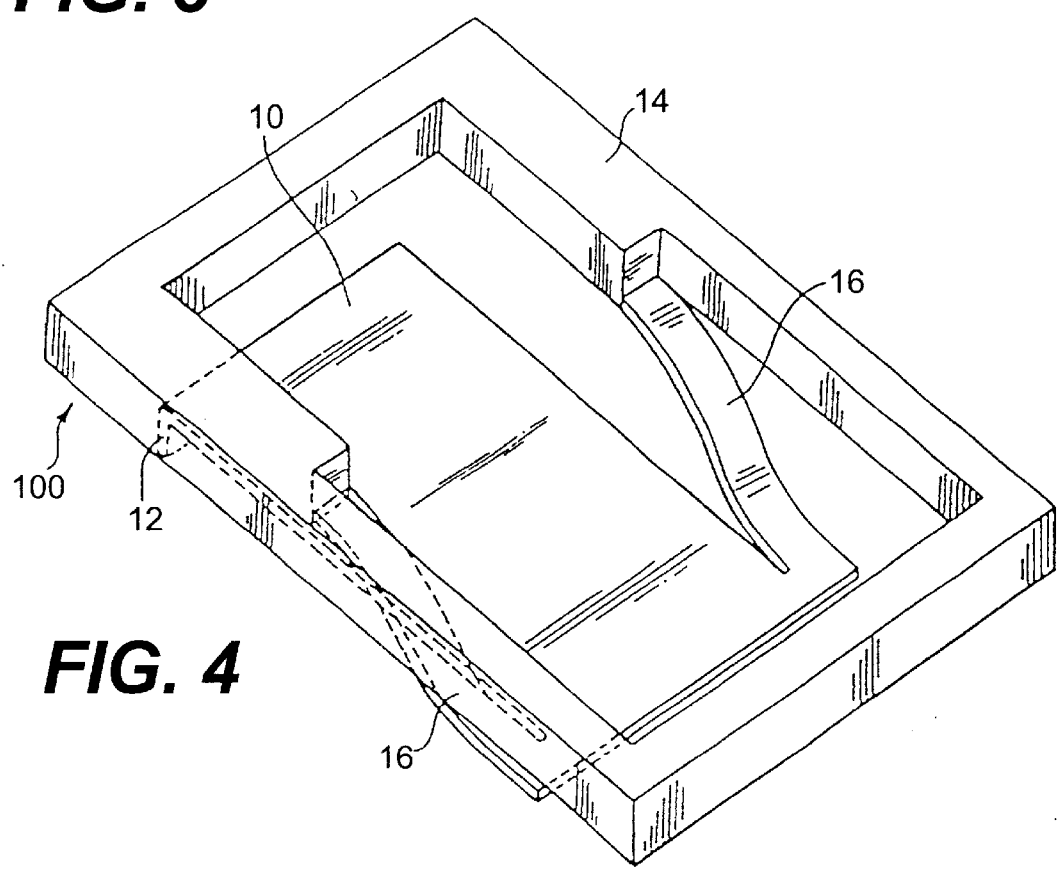
Figure 5:
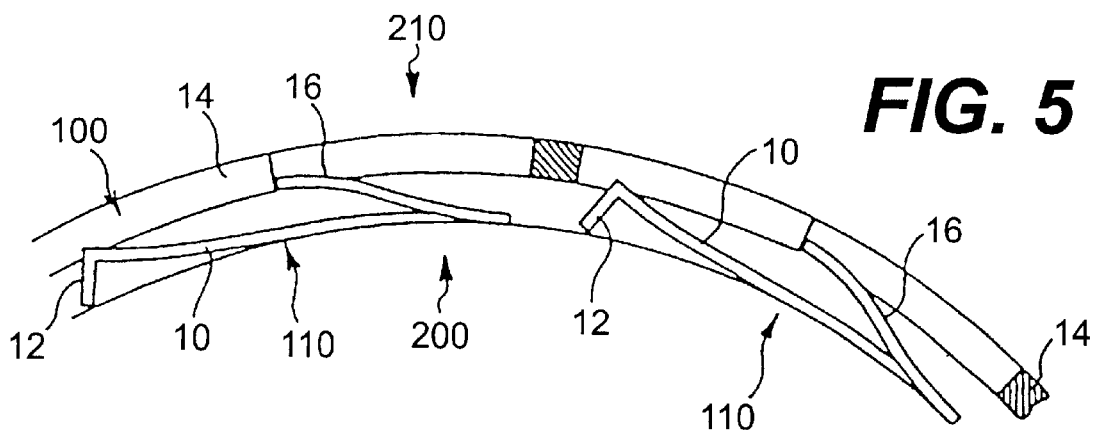
Figure 6:
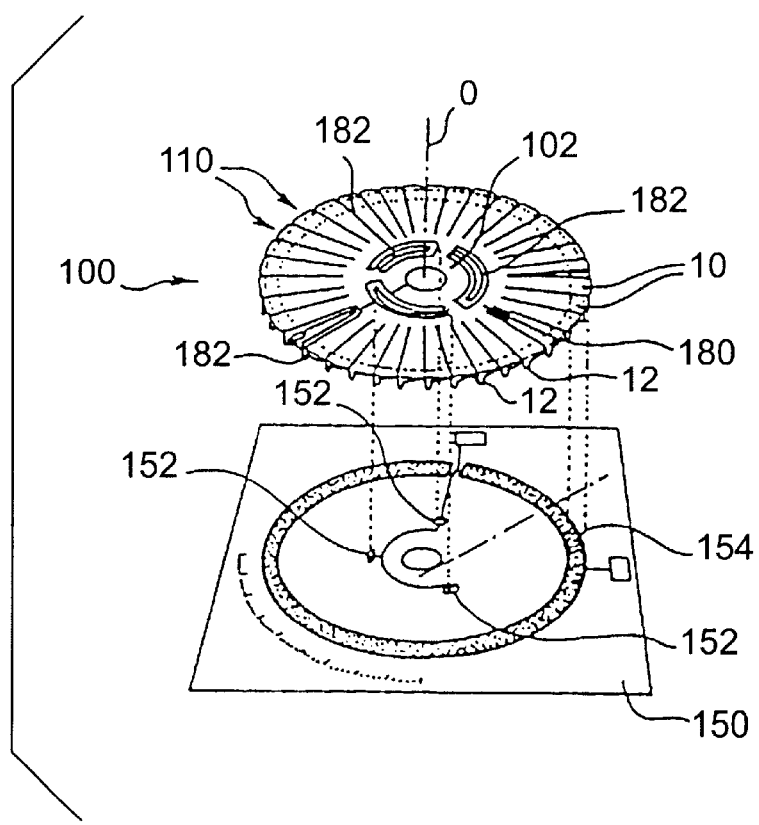
Figure 7:
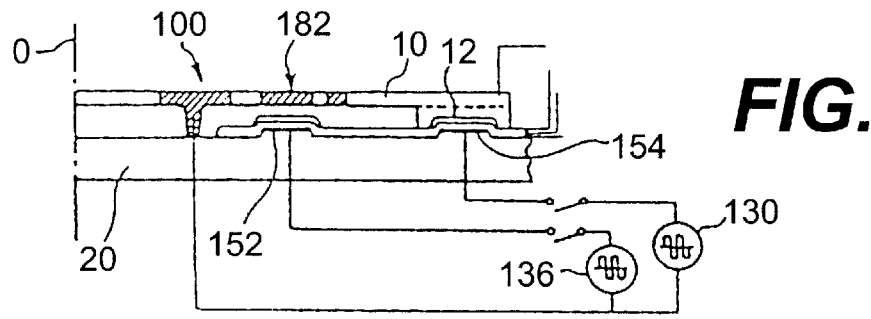
Figure 8:
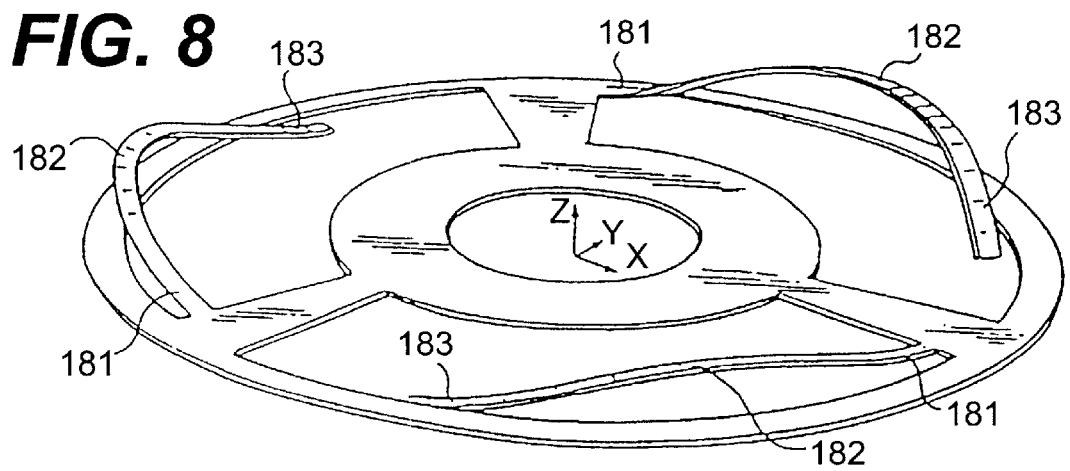
Figure 11:
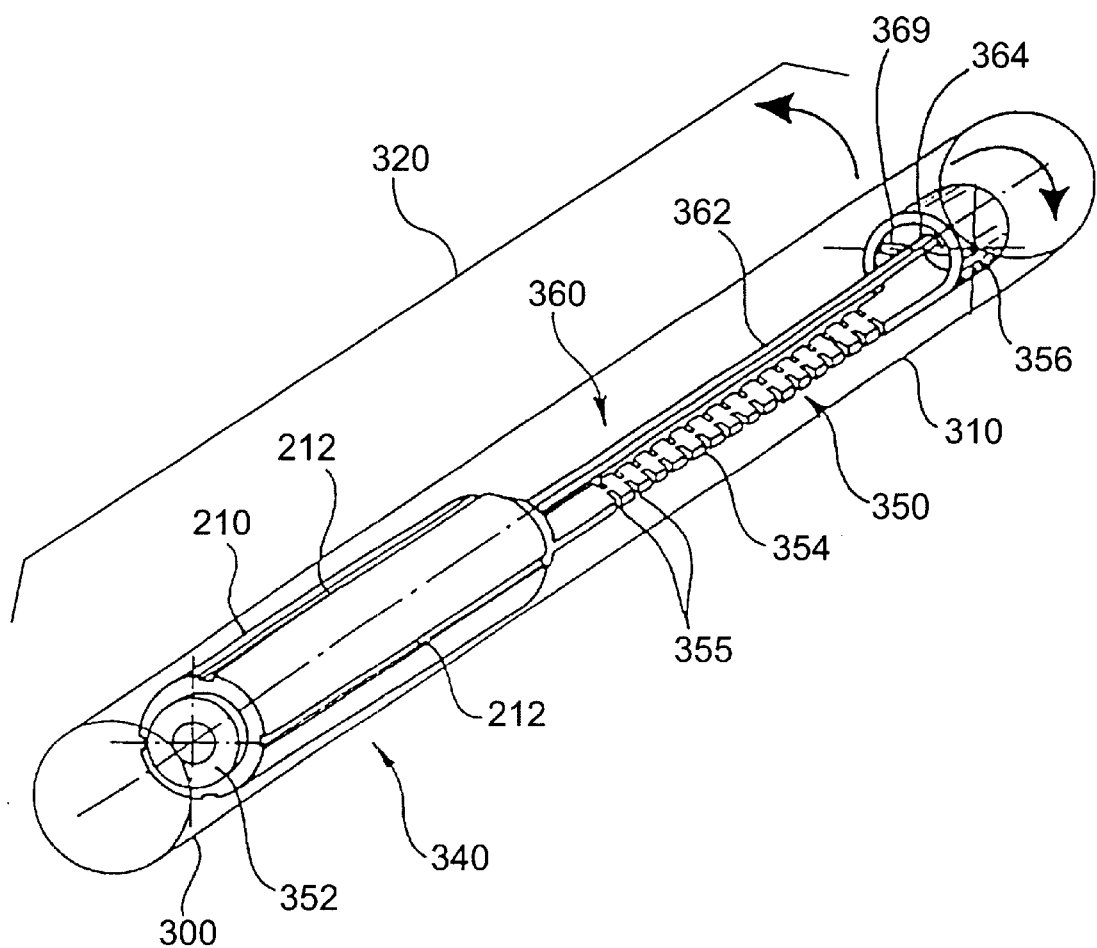
Figure 12:
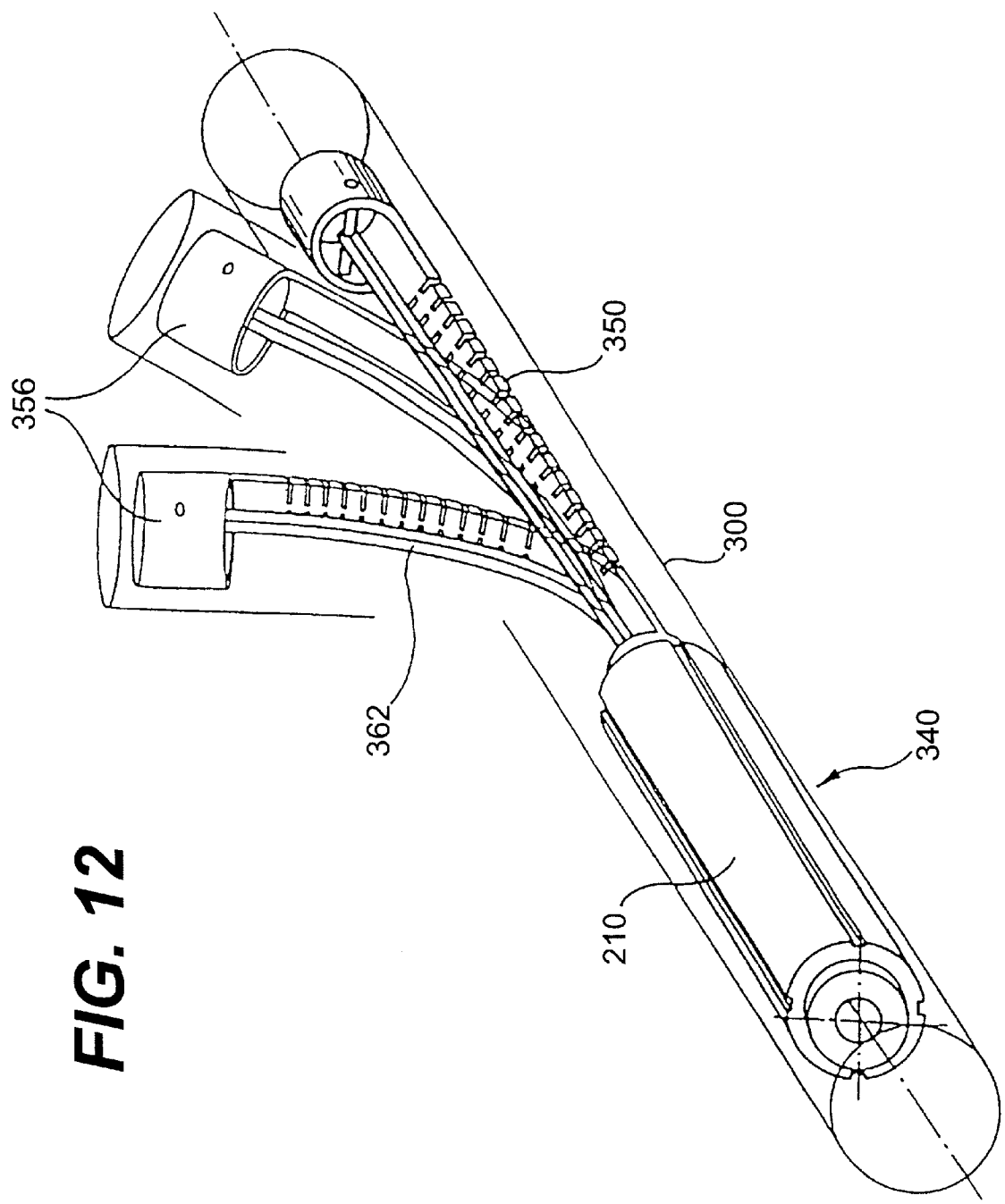
Figure 13:
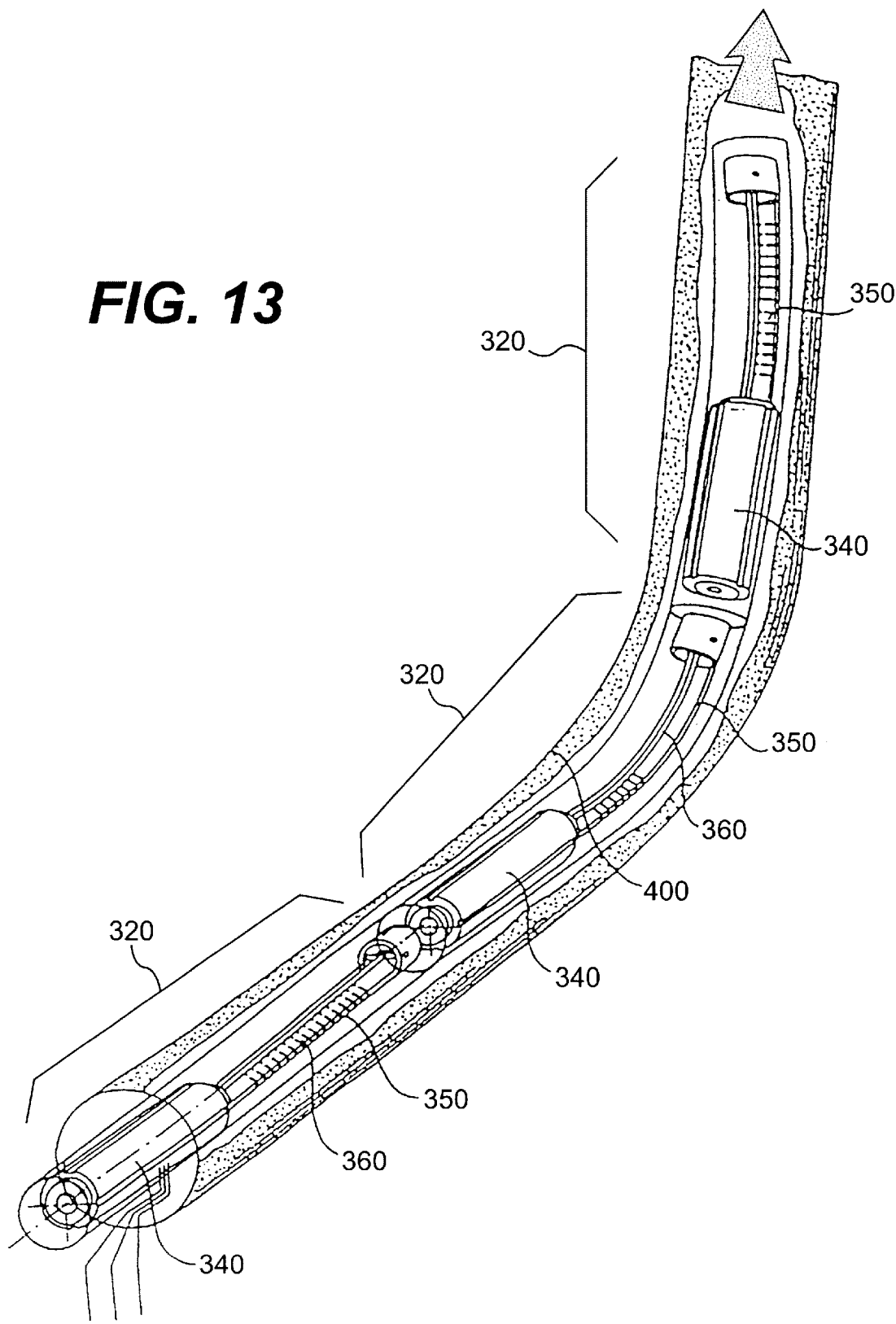

Other characteristics, objects and advantages of the present invention will become apparent on reading the detailed description which follows and in conjunction with the appended drawings, given by way of nonlimiting examples and in which:

FIGS. 1A to 1D described earlier diagrammatically illustrate the general structure and the operation of a conventional SDA, FIG. 2 diagrammatically illustrates a procedure for automatically detaching an SDA sheet from its support substrate, in accordance with the present invention, FIG. 3 diagrammatically shows a procedure for winding an SDA sheet in accordance with the present invention, around a tubular drive shaft, FIG. 4 diagrammatically shows a mechanical architecture of an elementary cell of SDAs in accordance with the present invention, FIG. 5 diagrammatically shows an SDA sheet in accordance with the present invention, positioned level with an interface between a rotor and a bedplate, FIGS. 6, 7 and 8 respectively represent an annular motor in accordance with the present invention, a partial cross-sectional view thereof, associated with its electrical control means and a diagrammatic depiction of a torque sensor integrated with this annular motor, FIG. 9 represents a perspective diagrammatic view of a microcatheter in accordance with the present invention, implementing a plurality of SDA actuators of the aforesaid type, FIG. 10 represents a longitudinal sectional view of the same catheter, FIG. 11 represents a basic module of such a catheter, FIG. 12 illustrates the deformation of such a module under the effect of an actuator based on a shape memory material, and FIG. 13 diagrammatically shows the use of such a catheter in accordance with the present invention in a blood vessel.

The known general structure of SDAs will not be described in detail hereinbelow.

Likewise for their fabricating technology. This technology derived from the technology for fabricating integrated circuits is in fact known to the person skilled in the art.

However, an exemplary process for fabricating an SDA sheet according to the present invention will be described hereinbelow.

The nominal dimensions of an SDA are typically of the order of a few tens of micrometers square. Within the framework of the present invention it is thus possible to envisage hundreds or even thousands of SDAs juxtaposed on an area of the order of a mm².

Preferably, within the framework of the present invention, the SDAs are made by chemical machining of thin sheets of doped polysilicon. Their configuration may form the subject of numerous variants. The same holds for the conditions of connection of the SDAs to the fabric of the sheet, the discretization of the sheet into elementary cells (number of SDAs per unit area) and the area of the sheet.

As indicated earlier within the framework of the present invention, in order to allow addition of the elementary forces generated by each SDA, the latter are subjected to an external mechanical prestress, preferably in the form of a bias voltage at rest, which imposes a permanent controlled flexion on the plate 10 of each SDA.

As indicated earlier, within the framework of the present invention, there is furthermore provision for means adapted for ensuring that the entire driving force emanating from the collective behavior of the SDAs is communicated to the external load.

To do this, the SDA sheet is preferably placed in the mechanical clearance between two solid bodies articulated together.

The SDA sheet can thus be placed between the substrate on which said SDA sheet has been made, and an attached solid body.

However, within the framework of the present invention, the SDA sheet is preferably separated firstly from its support substrate, then inserted into the aforesaid mechanical clearance existing between two solid bodies articulated together.

The polysilicon sheets comprising a colony of SDAs, in accordance with the present invention, exhibit high flexibility once they are detached from the silicon substrate on which they were chemically machined.

It is therefore possible to provide various solutions for transferring these sheets to their site of use.

According to one particularly advantageous implementation of the present invention, illustrated in FIG. 2, the detaching of the sheet comprising the SDAs, from its support substrate, is effected by virtue of flexion bars distributed at the periphery of the sheet.

Of course, as a variant, such flexion bars may be provided at another location on the sheet, for example within its mass, and not only at its periphery.

FIG. 2 thus depicts a flexible polysilicon sheet 100 comprising a large number of distributed elementary SDAs 110. This sheet 100 rests on the silicon substrate 150 on which said sheet 100 has been machined.

This sheet 100 comprises two parallel flexion bars 120 disposed respectively along two opposite edges of the sheet 100. The flexion bars 120 are separated over their length, from the mass of the sheet 100 by virtue of longitudinal cutouts 122 formed between said bars 120 and the central body of the sheet 100. The flexion bars 120 are thus machined from the mass of the sheet 100. However, the flexion bars 120 remain secured, via one of their ends, to this central body of the sheet 100.

When the first rows of SDAs, transverse to the aforesaid lateral edges and to the flexion bars 120 as well as opposite the zones of connection of said bars 120 to the sheet 100, are activated, the sheet 100 advances in the direction illustrated by the arrow referenced D in FIG. 2. To do this, a voltage can be applied between the plates 10 of the SDAs 110 concerned and an electrode buried in the substrate 150.

Thus, if the flexion bars 120 are conversely held in position with respect to the substrate 150 at least over part of their length, the displacement of the sheet 100 gives rise to a flexion of the bars 120 in a direction orthogonal to the plane of the substrate 150.

Also, as may be seen in FIG. 2, this flexion of the bars 120 causes the detaching of the sheet 100 from the substrate 150.

The holding of the bars 120 with respect to the substrate 150 can be achieved by numerous means. Preferably within the framework of the present invention this holding is itself achieved by virtue of electrostatic forces. To do this, preferably, as may be seen in FIG. 2, specific electrodes 160 are provided on the substrate 150, facing the bars 120. The application of an excitation voltage between these electrodes 160 and the bars 120, by means of a generator 132, thus makes it possible to push the bars 120 flat against the electrodes 160.

More precisely still, according to the preferred embodiment illustrated in the appended FIG. 2, several discrete electrodes 160 distributed facing the bars 120 are provided. Also, each of these electrodes 160 can be energized selectively by the generator 132, by way of a gang of respective switches 134. Thus, the selective closing of a chosen one or of several switches 134 makes it possible to select the energized electrode or electrodes 160 and consequently to control the zone of the bars 120 which is held on the substrate 150.

The inventors have shown that with this technique radii of curvature of a few tens of microns can be obtained on polysilicon sheets 100.

The sheet 100 comprising the SDAs 110 can thus be relocated to any desired site of use.

Illustrated in FIG. 3 is the relocating of a sheet 100 onto a movable motor element in the form of a drive shaft 200 which forms a support for the sheet 100.

This shaft 200 can itself form the subject of numerous embodiments. According to the particular and nonlimiting embodiment illustrated in FIG. 3, it involves a tubular shaft whose external envelope is a cylinder of revolution.

To ensure the transfer of the sheet 100 onto the shaft 200, the latter is placed on the substrate 150 level with the detached end of the sheet 100. The shaft 200 is then displaced under the sheet 100 as the latter is detached, as illustrated by the arrow illustrated F in FIG. 3. Simultaneously, preferably, the shaft 200 is accorded a rotational motion about its axis (as shown diagrammatically by the arrow R in FIG. 3) so that the shaft 200 will brace the sheet 100 as it detaches, without relative displacement between the surface of the shaft 200 and the sheet 100. Thus the sheet is progressively transferred, with no risk of damage, to the shaft 200.

The winding of the sheet 100 onto the shaft 200 is made easier if one simultaneously utilizes electrostatic attraction toward the drive shaft 200 itself.

To do this, the polysilicon sheet 100 can be subjected to a potential of the order of from 100 to 200 V peak while the drive shaft is grounded (or vice versa). Of course, an electrically insulating layer must be provided between the sheet 100 and the shaft 200. To this end, the shaft 200 can be made for example from a surface-oxidized electrically conductive material.

The present invention is in no way limited to the embodiment of a tubular motor as described in conjunction with FIG. 3. It can find application in a large number of configurations, such as for example in linear motors.

Moreover, depending on the orientation given to the SDAs, over the rows and columns of one and the same sheet, it is possible to make motors with several degrees of freedom.

Thus, for example, by utilizing two series of SDAs possessing orthogonal orientations, it is possible to make X-Y type plane translators. It is also possible to make motors of the latch type associating a rotational degree of freedom with a translational degree of freedom.

The insertion of the sheet 100 comprising the SDAs 110 at the interface between the drive shaft 200 and an associated external bedplate, can be achieved in various ways.

Preferably, in a first phase, the sheet 100 is subjected to a potential of the order of 100 V while the drive shaft 200 is grounded. The sheet 100 is therefore secured to the drive shaft 200, thus affording it the necessary rigidity for subsequently resisting the forces of insertion of the drive shaft into the bedplate.

The insertion of the drive shaft into its housing is then carried out.

Next, in a subsequent phase, the sheet 100 is locked with respect to the aforesaid housing so as to permit the relative motion of the drive shaft 200 with respect to the bedplate. To satisfy this locking the bedplate of the motor is in turn grounded with the aim of attracting the framework of the SDA sheet 100.

The rotational locking of the sheet 100 is therefore guaranteed by an electrostatic force field at the sheet 100/bedplate interface, as well as by the dry friction induced by the contact of the sheet 100 on the bedplate. The sheet 100 must be dimensioned (in terms of thickness in particular) so that the framework of the sheet 100 is attracted naturally by the bedplate, while the SDAs 110 remain attracted by the drive shaft 200.

To do this, each plate 10 forming an SDA is supported elastically in a framework 14 created in the sheet 100. For example as illustrated in FIG. 4, each plate 10 forming an SDA is supported by a framework 14 created in the sheet 100 by way of two parallel suspension bars 16. The latter join a respective longitudinal edge of the plate 10, opposite the strut 12, and the framework 14. The suspension bars extend perpendicularly to the direction of the strut 12.

In FIG. 5, the bedplate of the motor which surrounds the drive shaft 200 is referenced 210. Here again an electrically insulating layer must be provided between the electrically conductive bedplate 210 and the frameworks 14. This insulating layer can be obtained by oxidation of the internal surface of the bedplate 210.

Once it has been fixed in this way to the bedplate 210, the sheet 100 plays the role of stator.

Moreover, the aforesaid suspension bars 16 are preferably adapted so as to allow a sizeable radial displacement of the SDAs in relation to the framework 14 and thus to make it possible to compensate for the uncertainty relating to the inevitable mechanical clearance at the drive shaft 200/bedplate 210 interface.

Indeed, the standardized mechanical fabricating tolerances of macroscopic devices guarantee at best a mechanical clearance with an uncertainty of the order of some ten microns for a coupling 1 mm in diameter, i.e. an uncertainty which is far greater than twice the thickness of the SDA sheet 100.

The suspension bars 16 thus allow radial accommodation of the sheet 100 in the bedplate 210, so that the frameworks 14 are locked against the bedplate 210, while the struts 12 of the SDAs bear on the drive shaft 200.

The potential applications of the present invention are numerous. They relate in particular to the motorization of micromachines from the micrometer scale up to the millimeter scale.

It will be noted that the SDA sheets 100 can be inserted naturally into surface mechanical links exhibiting an operating clearance.

Thus, the SDA sheets 100 occupy a zero volume from the point of view of effective bulk. The present invention consequently makes it possible to make motors exhibiting a much greater volume/power factor than any existing system.

Moreover, insofar as the SDA sheets occupy a zero effective volume, it is possible to integrate them readily into mechanical links of a mechanism without affecting its mechanical architecture.

Likewise, the SDA sheets 100 in accordance with the present invention can be integrated into mechanical architectures of a traditional articulation, without additional bulk, and thus give rise to the infrastructure of a motor. The mechanical links then produce mechanical energy, whereas traditionally they have always dissipated it by reason of the dry friction at the interface of the solid bodies.

Represented in FIGS. 6 to 8 is a variant according to which the motor is of the annular type, that is to say it comprises a plane sheet 100 comprising a large number of SDAs 110, in the shape of a disk transverse to its axis of rotation O.

Such a motor is thus of two-dimensional type as opposed to the motor described earlier of three-dimensional type.

The sheet 100 which constitutes a rotor comprises a large number of SDAs 110 arranged radially from a central hub 102.

Typically but not limitingly, the rotor 100 can thus comprise 36 SDAs equidistributed about the axis of rotation O. The struts 12 of each of the plates 10 in the shape of a ring sector, extend along a longitudinal edge of these plates, along a radius pitched from the axis of rotation O, and preferably over only a part of the radial extension of these ring sectors, as may be seen in particular in FIGS. 6 and 7.

The rotation of the rotor about the axis O is achieved by virtue of a continuation of deformation of the plates 10, in accordance with the principle described earlier in conjunction with FIGS. 1, by virtue of pulses applied by a generator 130 between the plates 10 and an electrode 154 integrated into the support 150 forming a stator on which the rotor is disposed.

Furthermore, the motor illustrated in FIGS. 6 to 8 comprises a rotational torque sensor 180. The latter is arranged at the center of the sheet 100.

This sensor 180 comprises at least one inwardly curved beam 182, centered about the axis of rotation O, one end 181 of which is secured to the sheet 100, while the other end 183 of the beam 182 is free with respect to said sheet 100.

According to the embodiment illustrated in FIG. 6, the sensor 180 comprises three beams 182 equidistributed about the axis of rotation O of the rotor.

The beams 182 extend in the direction of rotation from the end 181 linked to the sheet 100.

They are preferably formed by chemical machining in the mass of the sheet 100 and of circular general shape, in the form of a ring sector.

When no force is exerted on the beams 182, the latter are contained in the plane of the sheet 100 and consequently no external braking torque is applied to the rotor 100.

However, if the free end 183 of the beams 182 is pushed flat against the support 150 of the rotor which forms a stator, the beams 182 are subjected to a force which causes them to bend, as shown diagrammatically in FIG. 8. Also, the amplitude of this bending depends directly on the driving torque generated by the SDAs. Thus, measurement of the amplitude of the deformation of the beams 182 makes it possible to measure the driving torque of the SDAs directly.

The beams 182 can thus be pushed flat onto the support 150 by electrostatic forces resulting from the application of a suitable voltage applied by a generator 136 between each beam 182 and electrodes 152 formed on the support 150 facing the displacement path of the beams 182.

Illustrated under the reference 154 in FIG. 6 is an annular electrode formed on the support 150, facing the displacement path of the struts 12. This electrode 154 serves as a driving electrode and allows the application of an excitation voltage between this electrode 154 and the plates 10 of the SDAs, with the aid of the generator 130.

The structure illustrated in FIG. 6 allows the construction of motors having for example a diameter of the order of 500 micrometers and a total height of a few micrometers.

An exemplary process for fabricating an SDA sheet in accordance with the present invention will now be described.

A 20 Ωcm n-type silicon wafer is prepared by cleaning in a buffered hydrofluoric acid solution. After rinsing with water and drying under $N_2$, the wafer is thermally oxidized at 1100° C. under $O_2$. A silicon oxide layer of the order of 0.35 micrometers thick is thus formed at the surface of the wafer. A polysilicon layer of the order of 0.5 micrometers thick is then deposited at 600° C. by LPCVD (Low Pressure Chemical Vapor Deposition). In order to reduce the resistivity of the polysilicon, phosphorus is implanted with a dose of $5 \times 10^{15}$ cm$^{-2}$ under an acceleration voltage of the order of 50 keV. After a first lithography step, the polysilicon layer is etched by $SF_6$ plasma so as to obtain a screen. A silicon-rich silicon nitride layer, of the order of 0.3 micrometers thick, is then deposited over the entire surface of the wafer at 800° C. by LPCVD. This layer protects the silicon oxide layer from etching by hydrofluoric acid in the course of a final sacrificial etching step.

A silicon oxide layer of the order of 2 micrometers thick is then deposited as sacrificial material at 600° C. by LPCVD.

After a second lithography step, strut molds are fashioned by reactive ion etching (RIE) with a $CHF_3 + O_2$ plasma. Of course, the depth of the strut molds previously constructed determines the height of the struts which will be formed. By controlling the etching time, a strut depth of the order of 1.5 micrometers can be obtained. Thus, a layer of the order of 0.5 micrometers is preserved between the nitride layer and the struts.

A third lithography step intended for making the contacts is then implemented. The LPCVD silicon oxide and the silicon nitride are removed by RIE under $CHF_3 + O_2$ plasma, so that a polysilicon layer deposited subsequently can locally contact the buried screen layer.

A polysilicon layer of the order of 1.0 micrometer thick intended thereafter to be fashioned as the main component is then deposited on the surface of the wafer at 600° C. by LPCVD. The SDA thickness is determined by the thickness of polysilicon. The structural polysilicon layer is doped by phosphorus implantation ($5 \times 10^{15}$ cm$^{-2}$ under an acceleration voltage of the order of 150 keV) and is thereafter fashioned by RIE under $SF_6 + SiCl_4$ plasma in the course of a fourth lithography step.

In order to relieve the residual stresses in the polysilicon, the wafer is heated in a neutral $N_2$ atmosphere at 1100° C. for 60 min, after deposition of a thin layer of silicon oxide by LPCVD. This silicon oxide layer serves to protect the polysilicon surface from nitrogen. Simultaneously, a diffusion and an activation of phosphorus in the polysilicon are carried out.

Finally, the wafer is immersed in a 50% HF bath so as to completely dissolve the sacrificial silicon oxide.

The wafer is then rinsed in a suitable solution (for example water+isopropyl alcohol) and dried under neutral atmosphere (for example nitrogen).

The SDA-based microactuator described above can find application in a large number of fields.

A nonlimiting exemplary application of this microactuator will now be described hereinbelow, in the embodiment of an active three-dimensional microcatheter, in conjunction with the appended FIGS. 9 to 13.

Thus, the appended FIGS. 9 to 13 illustrate an active catheter 300 of very small diameter (typically of the order of 1 mm), which, in a flexible envelope tube 310, comprises a series of modules 320 juxtaposed over the length of the tube 310.

The tube 310 can be formed for example from a polymer.

Each module 320 comprises a tubular electrostatic motor 340, an elastic rotor 350 and a shape memory actuator 360.

The electrostatic motor 340 can comply overall with the arrangements described earlier in conjunction with FIG. 5. Thus, the motor 340 preferably comprises an SDA sheet 100 placed in the mechanical clearance between the rotor 350 (which corresponds to the drive shaft 200 of FIG. 5) and a tubular bedplate 210.

The tubular bedplate 210 is furnished with longitudinal grooves 212 over its outer periphery, so as to allow the passage of insulated electrical supply wires 214 required for energizing the modules 320 situated downstream.

The rotor 350 can form the subject of numerous embodiments. According to the nonlimiting embodiment represented in FIGS. 9 to 13, the rotor 350 comprises two tubular end spans 352, 356 joined together by a longitudinal linking arm 354. The two tubular spans 352 and 356 have identical diameters. The linking arm 354 is preferably formed by machining a tube defining said spans 352 and 356 at its ends. Thus, the linking arm 354 preferably consists of a longitudinal bar which is straight at rest, in the shape of a sector of a cylinder whose radius of curvature corresponds to that of the spans 352 and 354. The span 352 of the rotor has a length substantially identical to the length of the bedplate 210, and said span 352 is introduced into this bedplate 210, so that the linking arm 354 and the second span 356 emerge out of the bedplate 210.

The rotor 350 at least at the level of the span 352 must be made from an electrically conductive material so as to allow the application of electrostatic forces to the SDA sheet 100. However, the external surface of the span 352 must be electrically insulating, for example by oxidation.

As indicated earlier, the rotor 350 must be sufficiently flexible to accept flexions under the effect of the control of the shape memory actuator 360.

As may be seen in FIG. 11, the linking arm 354 may as appropriate be furnished with a series of transverse notches 355 distributed over its length, between the two spans 352 and 356, and opening out onto its two longitudinal edges, or with any equivalent means, to obtain the appropriate flexibility.

The shape memory actuator 360 can also form the subject of numerous embodiments. According to the preferred embodiment illustrated in the appended figures, the actuator 360 is formed of a pin 362 centered on the rotor 350 and whose ends 364, 366 are respectively engaged in the spans 356 and 352 of the rotor.

The pin 362 can be formed for example from NiTi.

One of the ends of the pin 362 is fixed to one of the spans of the rotor, while the other end of the pin 362 is preferably fitted to the other span of the rotor, with freedom of longitudinal displacement with respect to the latter, so as to permit flexion of the pin 362 and of the rotor 350. By way of example, as illustrated in FIGS. 9 to 13, the end 364 of the pin 362 can thus be fixed to the tubular span 356 by a transverse stud 363. The other end 366 of the pin 362 is engaged in the central channel of a ball joint 367 positioned in the span 352.

As a variant, the pin 362 made from a shape memory material can be replaced with any equivalent structure, for example a wire or a helical spring.

The end span 356 of the rotor of a given module 320 is preferably joined to the bedplate 210 of the downstream module, both translationally and rotationally, by any suitable means shown diagrammatically under the reference 380 in the appended figures.

This microcatheter essentially operates as follows.

The shape memory actuator 360 makes it possible to control the bending of the drive shaft 350 with which it is associated, in a deformation plane previously defined by the geometric parameters of the elastic rotor 350, as is illustrated in FIG. 12.

The tubular motor 340 is for its part adapted for controlling the bending plane of the shape memory actuator 360.

This system is shown diagrammatically in FIG. 13 in a blood vessel 400.

The overall device obtained with the aid of the series association of several elementary modules 320 each combining an SDA actuator 340 and a shape memory actuator 360, makes it possible to cope with a large number of two-or three-dimensional configurations (plane curvatures with multiple, helical points of inflection, etc.), despite extremely simple connector engineering.

Thus, the modules 320 in accordance with the present invention combining an SDA actuator 340 and a shape memory actuator 360 can find numerous applications apart from the aforesaid microcatheter.

Of course, the present invention is not limited to the embodiments just described, but extends to all variants in accordance with the spirit thereof.

[1]"Controlled stepwise motion in polysilicon microstructures", T. Akiyama and K. Shono, J. MEMS, Vol. 2 N°3, pp 106–110, 1993;

[2]"Scratch drive actuator with mechanical links for self-assembly of three dimensional MEMS", T. Akiyama, D. Collard and H. Fujita, J. MEMS, Vol. 26 N°1, pp 10–17, 1997;

[3]"Self-assembled microactuated XYZ stages for Optical Scanning and Alignment", L. Fan, M. C. Wu, K. D. Choquette and M. H. Crawford, Transducers'97, International Conference on Solid-State Sensors and Actuators, pp319–322, Chicago, 1997.

What is claimed is:

1. Electrostatic microactuator based on distributed elementary actuators (110) each comprising a flexible plate or beam (10), furnished at one end with a projecting strut or pad (12), directed toward a substrate (20) covered with an insulating layer (22) and a generator (30) adapted for applying voltage pulses between the plate (10) and the substrate (20), characterized in that the electrostatic microactuator integrates a large number of such associated elementary actuators (110) and means (130) for applying individually, to the entirety of actuators (110), a homogeneous external pressure by using means guaranteeing a superposition of the driving forces generated by the various elementary actuators and, moreover, transferring to a common external load, the resultant of the driving forces emanating from the collective behavior of these same elementary actuators, the elementary actuators (110) being formed in a monolithic support sheet (100) placed in a mechanical clearance at the interface of two solid bodies (200, 210) articulated with respect to one another, in such a way that a framework of the sheet (100) is in contact with one of the solid bodies (210), while the elementary actuators (110) are in contact with the other body (200).

2. The microactuator of claim 1, wherein the means for applying a homogenous external pressure to the elementary actuators (110) are formed of means (130) able to apply a bias voltage at rest to the elementary actuators (110).

3. The microactuator of claim 1, wherein the support sheet (100) is flexible and one of the solid bodies (210) is formed of a bedplate, while the other body (200) is formed of a movable element.

4. The microactuator of claim 1, wherein the elementary actuator support sheet (100) is separated from its substrate before insertion into the mechanical clearance between the two solid bodies (200, 210).

5. The microactuator of claim 1, wherein each plate (10) forming an elementary actuator is supported elastically in a framework (14) created in the support sheet (100).

6. The microactuator of claim 5, wherein each plate (10) forming an elementary actuator is supported by the framework (14) created in the sheet (100), by way of two parallel suspension bars (16).

7. The microactuator of claim 1, wherein the plate or beam (10) is made of polysilicon.

8. The microactuator of claim 1, comprising from a few tens to a few thousand elementary actuators (110).

9. The microactuator of claim 1, wherein the support sheet (100) possesses flexion bars (120) such that when some flexion bars (120) are held on a substrate (150), at least some of the elementary actuators (110) are activated.

10. The microactuator of claim 1, further comprising a means (180) forming a force sensor, comprising at least one beam (182) integrated into the support sheet and adapted to be deformed upon actuation, said beam being associated with means for analyzing its deformation.

11. The microactuator of claim 1, wherein the elementary actuators (110) comprise chemically machined thin sheets of doped polysilicon.

12. The microactuator of claim 1, further comprising felxion bars (120), wherein the substrate comprises electrodes (160) facing the flexion bars (120) and a means to apply an excitation voltage between these electrodes (160) and the flexion bars (120) so as to push the flexion bars (120) flat against the electrodes (160).

13. The microactuator of claim 12, (120), wherein the electrodes are capable of being energized selectively so as to control the zone of the flexion bars (120) which is held on the substrate (150).

14. The microactuator of claim 1, wherein the monolithic support sheet (100) is placed on a tubular shaft (200).

15. The microactuator of claim 1, comprising two series of elementary actuators (110) possessing orthogonal orientations, to form an X-Y type plane translator.

16. The microactuator of claim 1, wherein the microactuator forms a latch type motor associating a rotational degree of freedom with a translational degree of freedom.

17. The microactuator of claim 1, wherein the microactuator forms an annular type motor.

18. The microactuator of claim 17, wherein the support sheet (100) comprises a large number of elementary actuators (110), in the shape of a disk transverse to its axis of rotation (0).

19. The microactuator of claim 18, wherein the sheet (100) constitutes a rotor and wherein the large number of elementary actuators (110) are arranged radially from a central hub (102), and wherein the strut (12) of each of the plates (10) is in the shape of a ring sector, and extends along a longitudinal edge of these plates, and along a radius pitched from the axis of rotation (0), and preferably over only a part of a radial extension of the ring sector.

20. The microactuator of claim 1, wherein the microactuator forms a torque sensor which comprises beams (182) wherein each beam (182) possesses an end (181) secured to the sheet (100), while the other end (183) of the beam (182) is free with respect to said sheet (100).

21. The microactuator of claim 20, wherein the sensor (180) comprises three beams (182) equidistributed about the axis of rotation (0) of a rotor.

22. The microactuator of claim 20, wherein the beams (182) extend in a direction of rotation from their end (181) secured to the sheet (100).

23. The microactuator of claim 20, wherein the beams (182) are pushed flat onto the support sheet (150) by electrostatic forces resulting from the application of a suitable voltage applied by the generator (136) between each beam (182) and electrodes (152) formed on the support sheet (150) facing a displacement path of the beams (182).

24. The microactuator of claim 1, wherein the microactuator is associated with a shape memory actuator (360).

25. The microactuator of claim 24, wherein said microactuator forms a motor (340) used in at least one module (320) which comprises a rotor (350) and the shape memory actuator, the shape memory actuator being formed of a pin (362) centered on the rotor (350).

26. The microactuator of claim 25, further comprising several modules (320) in series.

27. The microactuator of claim 26, wherein one end of the rotor of a given module (320) is joined to a bedplate (210) of a downstream module, both translationally and rotationally.

28. The microactuator of claim 25, wherein a tubular bedplate (210) of the motor (340) is furnished with longitudinal grooves (212) over its outer periphery, so as to allow the passage of insulated electrical supply wires (214) required for energizing modules (320) situated downstream.

29. The microactuator of claim 25, wherein the rotor (350) comprises two tubular end spans (352, 356) joined together by a longitudinal linking arm (354).

30. The microactuator of claim 29, wherein one of the ends of a pin (362) made of shape memory material is fixed to one of the spans of the rotor, while the other end of the pin (362) is fitted to the other span of the rotor, with freedom of longitudinal displacement with respect to the latter, so as to permit flexion of the pin (362) and of the rotor (350).

31. The microactuator of claim 30, wherein the one end (364) of the pin (362) is fixed to a rotor tubular span (356) by a transverse stud (363), while the other end (366) of the pin (362) is engaged in the central channel of a ball joint (367) positioned in a second rotor span (352).

32. The microactuator of claim 24, wherein the microactuator is placed in a flexible tube (310).

33. The microactuator of claim 1, wherein said microactuator is used in a microcatheter (300).

34. An active three-dimensional microcatheter comprising at least one microactuator of claim 1.

35. A process for fabricating the microactuator of claim 1, wherein the support sheet (100) comprises a large number of elementary actuators (110) and possesses flexion bars (120), and comprises a step of shaping the sheet by machining the flexion bars (120) from the substrate (150) such that when at least some of the elementary actuators (110) are activated, said sheet (100) is detached from the substrate.

36. The process of claim 35, wherein a movable motor element (200) is displaced under the sheet (100) as the latter is detached.

37. The process of claim 36, wherein the motor element (200) is accorded a rotational motion in the course of its displacement under the detached sheet (100) so that the motor element (200) will brace the sheet (100) as it detaches, without relative displacement between the surface of the motor element (200) and the sheet (100).

38. The process of claim 36, wherein an electrostatic attraction is generated between the sheet (100) and said motor element (200) while transferring the sheet onto the latter.

39. The process of claim 38, wherein the electrostatic attraction is generated by applying a voltage between the sheet (100) and said motor element (200).

40. The process of claim 35, wherein an electrostatic attraction is maintained between the sheet (100) and a movable element (200) forming a support for the sheet, and further including the step of inserting the movable element (200) into a bedplate (210), while after placing the element (200) in the bedplate, an electrostatic attraction is applied between the bedplate (210) and a framework of the sheet (100) so as to lock the body of the sheet against the bedplate (210) while allowing the activated struts (12) of the elementary actuators to bear on said movable element.

* * * * *

UNITED STATES PATENT AND TRADEMARK OFFICE
CERTIFICATE OF CORRECTION

PATENT NO. : 6,461,337 B1
DATED : October 6, 2002
INVENTOR(S) : Patrice Minotti et al.

It is certified that error appears in the above-identified patent and that said Letters Patent is hereby corrected as shown below:

Column 13,
Line 16, after "(120)" insert a comma.
Line 20, delete "(120),".
Line 42, after "plates" delete the comma.

Column 14,
Line 62, before "elementary" insert -- activated --.

Signed and Sealed this

Seventeenth Day of December, 2002

JAMES E. ROGAN
*Director of the United States Patent and Trademark Office*